United States Patent
Fujimoto et al.

(10) Patent No.: US 11,668,556 B2
(45) Date of Patent: Jun. 6, 2023

(54) SYSTEMS AND METHODS FOR GENERATING AND DISPLAYING OCT BLOOD FLOW SPEEDS BY MERGING MUTIPLE INTEGRATED SPATIAL SAMPLINGS

(71) Applicant: Massachusetts Institute of Technology, Cambridge, MA (US)

(72) Inventors: James G. Fujimoto, Medford, MA (US); Eric Michael Moult, Cambridge, MA (US); ByungKun Lee, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 773 days.

(21) Appl. No.: 16/611,011

(22) PCT Filed: May 4, 2018

(86) PCT No.: PCT/US2018/031030
§ 371 (c)(1),
(2) Date: Jan. 21, 2020

(87) PCT Pub. No.: WO2018/204748
PCT Pub. Date: Nov. 8, 2018

(65) Prior Publication Data
US 2020/0064118 A1   Feb. 27, 2020

Related U.S. Application Data

(60) Provisional application No. 62/501,869, filed on May 5, 2017.

(51) Int. Cl.
*G01B 9/02091* (2022.01)
*A61B 90/00* (2016.01)
(Continued)

(52) U.S. Cl.
CPC .......... *G01B 9/02091* (2013.01); *A61B 3/102* (2013.01); *A61B 3/107* (2013.01);
(Continued)

(58) Field of Classification Search
CPC ............ G01B 9/02091; G01B 9/02045; A61B 3/102; A61B 3/107; A61B 3/1233;
(Continued)

(56) References Cited

U.S. PATENT DOCUMENTS

| 7,365,856 B2 | 4/2008 | Everett et al. |
| 8,004,517 B1 | 8/2011 | Edelsbrunner et al. |

(Continued)

FOREIGN PATENT DOCUMENTS

| EP | 1118962 A1 | 7/2001 |
| WO | WO-2006/077107 A1 | 7/2006 |

(Continued)

OTHER PUBLICATIONS

Baumann et al., "Total Retinal Blood Flow Measurement with Ultrahigh Speed Swept Source/Fourier Domain ODT," Biomedical Optics Express, 2(6):1539-1552 (2011).
(Continued)

*Primary Examiner* — Mohammed A Hasan
(74) *Attorney, Agent, or Firm* — Alexander Akhiezer; Foley Hoag LLP (57) ABSTRACT

A computer-implemented method of imaging an object, and an optical coherent tomography (OCT) imaging system implementing same. The method comprises acquiring a three-dimensional optical coherence tomography (OCT) data set representing an object, wherein the OCT data set includes at least a first and a second three-dimensional data subsets, each element of the OCT data set having a respective sampling period, wherein at least a first element of the first data subset represents a point in space that is not
(Continued)

represented by any element of the second subset, and at least one element of the second subset has a sampling period different from the sampling period of the first element of the first subset; processing at least the first and the second data subsets according to at least one imaging modality, thereby generating at least a first and a second processed data subsets, each processed data subset representing the object; and generating a composite image representing the object based on at least the first and the second processed data subsets.

21 Claims, 7 Drawing Sheets (51) Int. Cl.
G16H 30/40 (2018.01)
A61B 3/10 (2006.01)
A61B 3/107 (2006.01)
A61B 3/12 (2006.01)
A61B 5/00 (2006.01)
A61B 5/02 (2006.01)
A61B 5/145 (2006.01)
A61B 5/1455 (2006.01)
G01B 9/02 (2022.01)
A61B 5/026 (2006.01)
A61B 5/0285 (2006.01)

(52) U.S. Cl.
CPC .......... A61B 3/1233 (2013.01); A61B 3/1241 (2013.01); A61B 5/0035 (2013.01); A61B 5/0066 (2013.01); A61B 5/02014 (2013.01); A61B 5/14535 (2013.01); A61B 5/14552 (2013.01); A61B 5/7425 (2013.01); A61B 90/39 (2016.02); G01B 9/02045 (2013.01); G16H 30/40 (2018.01); A61B 5/0261 (2013.01); A61B 5/0285 (2013.01); A61B 2090/3937 (2016.02)

(58) Field of Classification Search
CPC ... A61B 3/1241; A61B 5/0035; A61B 5/0066; A61B 5/02014; A61B 5/14535; A61B 5/14552; A61B 5/7425; A61B 90/39; A61B 5/0261; A61B 5/0285; A61B 2090/3937; A61B 3/0025; G16H 30/40; G16H 30/20; G06V 2201/03; G06V 20/69
USPC .......................................................... 600/318
See application file for complete search history.

(56) References Cited

U.S. PATENT DOCUMENTS

| | | | |
|---|---|---|---|
| 9,269,144 B2* | 2/2016 | Kraus | G06T 11/006 |
| 9,978,159 B2* | 5/2018 | Kraus | A61B 3/102 |
| 10,839,515 B2 | 11/2020 | Moult et al. | |
| 2005/0249398 A1 | 11/2005 | Khamene et al. | |
| 2006/0034374 A1 | 2/2006 | Park et al. | |
| 2008/0021882 A1 | 1/2008 | Pu et al. | |
| 2008/0100612 A1* | 5/2008 | Dastmalchi | A61B 3/102 345/418 |
| 2009/0005691 A1 | 1/2009 | Huang et al. | |
| 2009/0103049 A1 | 4/2009 | McLean et al. | |
| 2010/0166280 A1 | 7/2010 | Endo et al. | |
| 2010/0208201 A1 | 8/2010 | Knighton et al. | |
| 2011/0075946 A1 | 3/2011 | Buckland et al. | |
| 2011/0134394 A1* | 6/2011 | Srinivasan | A61B 5/0073 356/479 |
| 2011/0299034 A1 | 12/2011 | Walsh et al. | |
| 2014/0100449 A1* | 4/2014 | Begin | A61B 5/0073 600/424 |
| 2014/0160488 A1 | 6/2014 | Zhou | |
| 2016/0284103 A1 | 9/2016 | Huang | |
| 2017/0221203 A1 | 8/2017 | Iwase et al. | |
| 2020/0064118 A1 | 2/2020 | Fujimoto et al. | |
| 2020/0133182 A1 | 4/2020 | Haik et al. | |

FOREIGN PATENT DOCUMENTS

WO WO-2011/139895 A1 11/2011
WO WO-2018/204748 A1 11/2018

OTHER PUBLICATIONS

Brauff et al., "Angiography of the retina and the choroid with phase-resolved OCT using interval-optimized backstitched B-scans," Biomed. Opt. Express (2012).
Choi et al., "Ultrahigh-Speed, Swept-Source Optical Coherence Tomography Angiography in Nonexudative Age-Related Macular Degeneration with Geographic Atrophy," Ophthalmology, (2015).
Choi et al., "Characterizing relationship between optical microangiography signals and capillary flow using microfluidic channels," Biomed. Opt. Express, 7:2709-2728 (2016).
International Preliminary Report on Patentability for International Application No. PCT/US2011/034572 dated Nov. 8, 2012.
International Search Report and the Written Opinion for International Application No. PCT/US2011/034572 dated Sep. 14, 2011.
International Search Report and Written Opinion for International Application No. PCT/US2018/031030 dated Oct. 3, 2018.
Jaillon et al., "Variable Velocity Range Imaging of the Choroid with Dual-Beam Optical Coherence Angiography," Opt. Express 20:385-396 (2012).
Jonghwan et al., "Dynamic light scattering optical coherence tomography," Opt. Express, 20:22262-22277 (2012).
Kraus et al., "Combination of Multiple Motion Corrected OCT Volume Scans for Noise Reduction and Extraction of Arbitrary Cross-Sectional Images," ARVO Abstract Only, 2 pages, Retrieved from the Internet on Feb. 16, 2010 from http://www.abstractsonline.com/submit/SubmitPrinterFriendlyVersion.as . . . .
Kraus et al., "Motion Artifact Correction In OCT Volume Scans Using Image Registration," ARVO Abstract Only, 3 pages, Retrieved from the Internet on Apr. 12, 2009 from http://www.abstractsonline.com/submit/SubmitPrint . . . .
Lee, J. et al., "Dynamic light scattering optical coherence tomography," Opt. Express, 20:22262-22277 (2012).
Ricco et al., "Correcting Motion Artifacts in Retinal Spectral Domain Optical Coherence Tomography via Image Registration," Medical Image Computing and Computer-Assisted Intervention a Miccai 2009, Springer Berlin Heidelberg, Berlin, Heidelberg, pp. 100-107, XP019130304 (2009).
Shi et al., "Wide Velocity Range Doppler Optical Microangiography Using Optimized Step-Scanning Protocol with Phase Variance Mack," Journal of Biomedical Optics, 18(10):106015 (2013).
Tokayer et al., "Blood Flow Velocity Quantification Using Split-Spectrum Amplitude-Decorrelation Angiography with Optical Coherence Tomography," Biomedical Optics Express 4:1909-1924 (2013).
Tolliver et al., Carnegie Mellon, UPMC Eye Center "An In-painting Method for Combining Multiple SD-OCT Scans With Applications in Z-Motion Recovery," Noise Reduction and Longitudinal Studies, Tuesday, May 5, 2009, 1 page.
Zawadzki et al., "Correction of motion artifacts and scanning beam distortions in 30 ophthalmic optical coherence tomography imaging," Progress in Biomedical Optics and Imaging, Proceedings of SPIE—Ophthalmic Technologies XVII 2007 SPIE US, 6426:1-11 (2007).

* cited by examiner

SYSTEMS AND METHODS FOR GENERATING AND DISPLAYING OCT BLOOD FLOW SPEEDS BY MERGING MUTIPLE INTEGRATED SPATIAL SAMPLINGS

RELATED APPLICATION

This application is the U.S. National Stage of International Application No. PCT/US2018/031030, filed May 4, 2018, which designates the U.S., published in English, and claims the benefit of U.S. Provisional Application No. 62/501,869, filed May 5, 2017. The entire teachings of the above applications are incorporated herein by reference.

GOVERNMENT SUPPORT

This invention was made with government support under grant number FA9550-12-1-0499 and FA9550-15-0473 awarded by the Air Force Office of Scientific Research (AFOSR), and R44-EY022864 and R01-EY011289 awarded by the National Institutes of Health (NIH). The government has certain rights in the invention. The government has certain rights in the invention.

BACKGROUND OF THE INVENTION

A variety of ocular pathologies are caused by and/or result in alterations of the retinal and/or choriocapillaris vasculatures. For example, age-related macular degeneration (AMD) and diabetic retinopathy (DR), leading causes of blindness and severe vision loss in developed countries, are associated with alterations of the retinal and choriocapillaris vasculatures. Retinal and choroidal vasculatures have traditionally been imaged with dye-based methods, such as fluorescein angiography and indocyanine green angiography. More recently, optical coherence tomography (OCT) methods, including Doppler OCT, dynamic light scattering (DLS) OCT, and OCT angiography (OCT-A) have emerged as a noninvasive method for volumetrically visualizing retinal and choroidal vasculatures in vivo.

SUMMARY OF THE INVENTION

In a first example embodiment, the present invention is a computer-implemented method of imaging an object. The method comprises acquiring a three-dimensional optical coherence tomography (OCT) data set representing an object, wherein the OCT data set includes at least a first and a second three-dimensional data subsets, each element of the OCT data set having a respective sampling period, wherein at least a first element of the first data subset represents a point in space that is not represented by any element of the second subset, and at least one element of the second subset has a sampling period different from the sampling period of the first element of the first subset; processing at least the first and the second data subsets according to at least one imaging modality, thereby generating at least a first and a second processed data subsets, each processed data subset representing the object; and generating a composite image representing the object based on at least the first and the second processed data subsets.

In a second example embodiment, the present invention is an optical coherent tomography (OCT) imaging system. The system comprises a memory configured to store a three-dimensional optical coherence tomography (OCT) data set representing an object, wherein the OCT data set includes at least a first and a second three-dimensional data subsets, each element of the OCT data set having a respective sampling period, wherein at least a first element of the first data subset represents a point in space that is not represented by any element of the second subset, and at least one element of the second subset has a sampling period different from the sampling period of the first element of the first subset; a computing module, configured to process at least the first and the second data subsets according to at least one imaging modality, and thereby to generate at least a first and a second processed data subsets, each processed data subset representing the object; and to generate a composite image representing the object based on at least the first and the second processed data subsets.

In a third example embodiment, the present invention is a non-transitory computer-readable medium having thereon a sequence of instructions, which, when executed by a processor, cause a memory to store a three-dimensional optical coherence tomography (OCT) data set representing an object, wherein the OCT data set includes at least a first and a second three-dimensional data subsets, each element of the OCT data set having a respective sampling period, wherein at least a first element of the first data subset represents a point in space that is not represented by any element of the second subset, and at least one element of the second subset has a sampling period different from the sampling period of the first element of the first subset; cause a computing module to process at least the first and the second data subsets according to at least one imaging modality, thereby generating at least a first and a second processed data subsets, each processed data subset representing the object; and to generate a composite image representing the object based on at least the first and the second processed data subsets.

In a fourth example embodiment, the present invention is a computer-implemented method of imaging an object, comprising: acquiring a three-dimensional optical coherence tomography (OCT) data set representing an object, each element of the OCT data set having a respective sampling period, wherein the sampling period of at least a first element of the data set is different from the sampling period of at least a second element of the data set; and generating an image representing the object based on at least the first and the second elements.

In a fifth example embodiment, the present invention is an optical coherent tomography (OCT) imaging system, comprising a memory configured to store a three-dimensional optical coherence tomography (OCT) data set representing an object, each element of the OCT data set having a respective sampling period, wherein the sampling period of at least a first element of the data set, the first element representing a first point in space, is different from the sampling period of at least a second element, of the data set, the second element representing a second point in space; and a computing module configured to generate an image representing the object based on at least the first and the second elements.

In a sixth example embodiment, the present invention is a non-transitory computer-readable medium having thereon a sequence of instructions, which, when executed by a processor cause a memory configured to a three-dimensional optical coherence tomography (OCT) data set representing an object, each element of the OCT data set having a respective sampling period, wherein the sampling period of at least a first element of the data set, the first element representing a first point in space, is different from the sampling period of at least a second element, of the data set, the second element representing a second point in space; and cause a computing module configured to generate an image representing the object based on at least the first and the second elements.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

The teachings of all patents, published applications and references cited herein are incorporated by reference in their entirety.

Optical Coherence Tomography

Optical coherence tomography (OCT) acquires cross-sectional images and volumetric data sets by measuring the echo time delay and magnitude of backscattered or back-reflected light from inside an object material or biological tissue ("a signal"). Axial scan or "A-scan" collects information about the object structure as a function of depth. A-scan is performed by directing an optical beam along a direction that transverses the object's surface, i.e. into the object, and measuring the echo time delay of backscattered or back-reflected light.

Cross-sectional images or "B-scans" can be generated by scanning the optical beam in a plane (not necessarily flat) that includes at least one A-scan, for example, moving the optical beam in a direction approximately parallel to the object's surface, and performing successive axial scan (A-scan) measurements. A B-scan generates a two dimensional array of data points that represents the backscattering or back-reflection in a plane within the object. This two dimensional information can be displayed as a false color or grey scale image.

Volumetric (i.e. three-dimensional) 3D-OCT or three-dimensional OCT datasets can be generated by performing successive B-scans in different planes, for example, using a raster type scan pattern. In general, a three-dimensional OCT dataset is generated by sweeping a beam of light over an object while recording A-Scan data. The beam is swept according to a trajectory as defined by a scan pattern. The scan pattern positions the beam at positions on the imaged object at points in time from which A-scan data is recorded successively. It is generally the case that the OCT data sets are composed of individual pixels or voxels in a 1D, 2D, or 3D data set The elements of three-dimensional data set are traditionally referred to as voxels.

Additionally, one of ordinary skill in the art of OCT will appreciate that, in general, an OCT dataset can contain multiple data channels, such as amplitude, intensity, phase, polarization, spectroscopic information, and Doppler shift, among others.

OCT can be performed using different embodiments including 1) an interferometer with a broadband light source and scanning optical reference delay line (known as time domain detection), 2) an interferometer with a broadband light source and a spectrometer for signal detection (known as Fourier/spectral domain OCT, spectral radar, or by other names) or 3) an interferometer with a frequency swept light source (known as swept source/Fourier domain OCT, optical frequency domain imaging, or by other names).

Optical Coherence Tomography Measurements of Blood Flow Speeds

Figure 1:
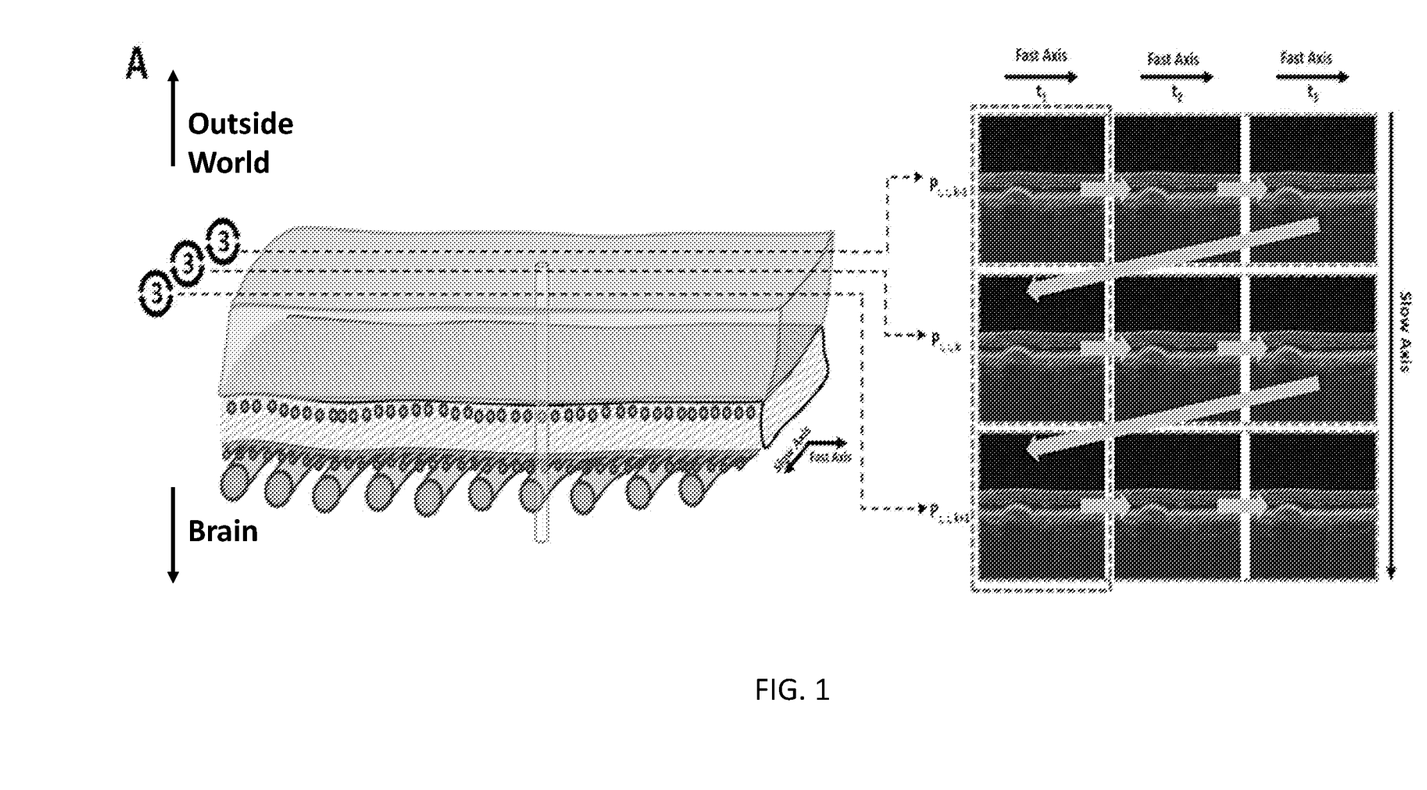
FIG. 1 is a schematic diagram representing acquisition of optical coherence tomography (OCT) data according to one example embodiment described herein.

There have been a variety of optical coherence tomography (OCT) methods for studying blood flow both in the eye, as well as other tissues. Currently, in ophthalmology, the most popular such method is OCT angiography (OCT-A). OCT-A has its roots in Doppler OCT, a technique that measures the Doppler shifts caused when blood cells scatter the OCT light beam, and uses these shifts to estimate blood flow speed/velocity (See, e.g., Izatt, J. A., Kulkarni, M. D., Yazdanfar, S., Barton, J. K., & Welch, A. J. (1997). In vivo bidirectional color Doppler flow imaging of picoliter blood volumes using optical coherence tomography. *Optics Letters*, 22(18), 1439-1441, the entire teachings of which are incorporated herein by reference.) As illustrated in FIG. 1, a typical OCT-A acquisition involves acquiring, for each slow axis B-scan position, repeated OCT B-scans. The beam can then be translated along a "slow axis" so as to acquire sets of repeated from different slow axis positions. In this way an OCT-A volume can be generated. The resulting B-scans can be schematically arranged in the image matrix of FIG. 1, where the thick orange arrows indicate time progression. While FIG. 1 illustrates a simple raster scanning protocol, OCT-A can be performed using a wide range of acquisition protocols. For example, repeated B-scans may be acquired radially, and the B-scan position may be rotated about some point. Furthermore, while in the example of FIG. 1, three repeated B-scans are at each slow axis position, the only requirement in OCT-A is that more than one repeated B-scans be acquired. As used herein, "B-scan" means a collection of two or more A-scans taken from distinct positions. Because the OCT light beams have a physical transverse width (the spot size), the optical fields from two distinct A-scan positions may overlap. This can happen, for example, in the case of oversampled scanning, which is commonly performed in OCT-A. As used herein, "repeated B-scans" means a collection of two or more B-scans in which at least one A-scan is common to all B-scans in the collection. It is noted that this meaning may be broader than that used in some literature.

Figure 2:
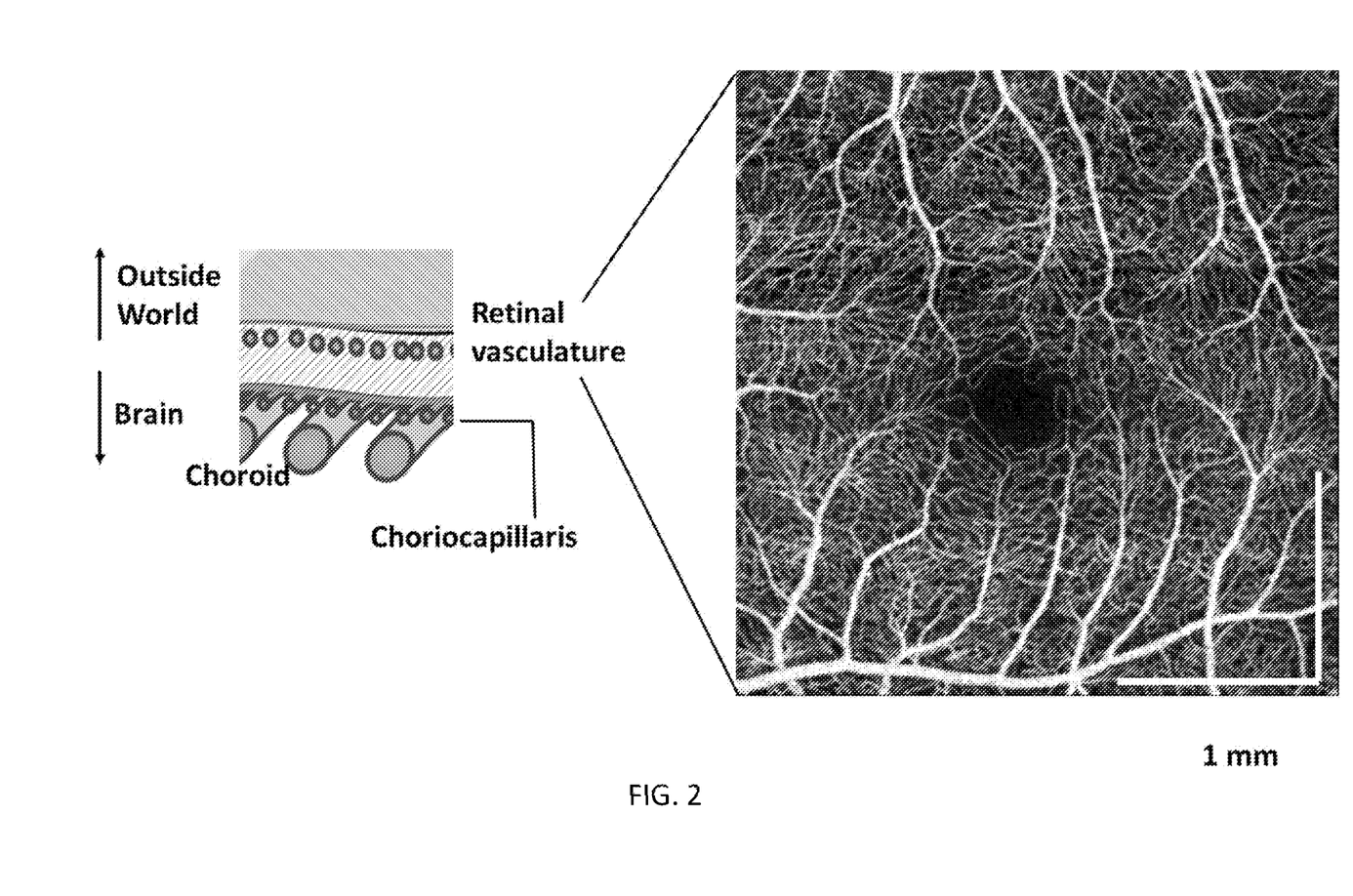
FIG. 2 is an example of an OCT angiography (OCT-A) image.

OCT-A is based on the idea that if the imaged tissue is stationary between repeated scans, the repeated B-scans will be identical, or very similar. If there is movement within the tissue, the repeated B-scans will differ due to this movement. In biological tissue, and in particular ocular tissue, this difference between repeated B-scans is often caused by moving blood cells, and can thus be used as an indicator of blood flow. Because blood flow is, typically, localized to vasculature, an OCT-A image of blood flow also delineates vascular structure. When applied to ophthalmological imaging, the OCT-A can generate images of ocular vasculatures (for example, retinal and choroidal vasculatures). An example OCT-A image of the retinal vasculature of a normal subject, flattened along the retinal depth direction, is illustrated in FIG. 2. Such a projection along the axial direction, parallel to the OCT beam, is referred to as an en face projection. The field of view of the OCT-A image in FIG. 2 is 3 mm×3 mm, and is centered at the fovea.

OCT-A is a promising modality for visualizing vasculature (e.g., presence, absence, or morphological alterations) in a variety of ocular diseases, including age-related macular degeneration and diabetic retinopathy. Compared to dye-based techniques, OCT-A is depth-resolved, non-invasive, acquired simultaneously with OCT, capable of resolving microvasculature, capable of visualizing retinal and choriocapillaris vasculatures, not obfuscated by dye leakage, and potentially quantitative. However, most OCT-A techniques have limited dynamic ranges, and provide and display limited information about the blood flow speeds within the imaged vasculature. Visualizing blood flow speeds, and related quantities, may be important when assessing diseases in which disease progression is linked to flow impairment, not just vasculature loss or morphological alterations. It may also be useful for assessing treatment responses, detecting diseases at early or sub-clinical stages, and/or for developing and/or evaluating endpoints for pharmaceutical trials. For example, a patient with choroidal neovascularization (CNV) may be injected with vascular endothelial grow factor inhibitors for treatment. Visualization and/or quantitation of the blood flow speeds and/or related quantities within, or surrounding, the lesion before and after injection may be useful for determining treatment efficacy, individualizing treatment strategies, and so on. Blood flow speeds may also be used for tracking the natural progressions of diseases that are caused by, and/or result in, blood flow alterations.

For example, knowledge of blood flow speeds may be useful for studying the relationship between the development/growth of geographic atrophy and choriocapillaris alterations. Or, as another example, knowledge of blood flow speeds may be useful for investigating possible relationships between neurodegenerative diseases, such as Alzheimer's disease, and blood flow speeds in the vasculature of the eye or brain. While there have been some proposed approaches to quantitate the OCT-A signal, OCT-A images are currently interpreted by most clinicians as showing the presence or absence of vasculature, rather than as showing data relating to blood flow speeds, with the OCT-A images interpreted in an almost binary manner. Thus, typically, OCT-A images are currently used to delineate vascular structures, rather than to provide information about blood flow within these vascular structures.

While OCT-A techniques often provide limited direct information about blood flow speeds, other OCT techniques provide information directly related to blood flow speeds. For example, Doppler OCT measures the velocity of the blood flow in the axial direction (i.e., parallel to the OCT beam), via measurements of Doppler shifts. Knowledge of the Doppler angle can allow for velocity measurements. There have also been demonstrations of Doppler OCT using multiple OCT beams, incident at different angles, to compute the blood flow speed (see, e.g., Haindl, R., Trasischker, W., Wartak, A., Baumann, B., Pircher, M., & Hitzenberger, C. K. (2016). Total retinal blood flow measurement by three beam Doppler optical coherence tomography. *Biomedical Optics Express,* 7(2), 287-301, the entire teachings of which are incorporated herein by reference). Other techniques, such as dynamic light scattering (DLS) OCT (see, e.g., Lee, J., Wu, W., Jiang, J. Y., Zhu, B., & Boas, D. A. (2012). Dynamic light scattering optical coherence tomography. *Optics Express,* 20(20), 22262-22277, the entire teachings of which are incorporated herein by reference), and eigenvalue decomposition velocimetry (see, e.g., Wang, R. K., Zhang, Q., Li, Y., & Song, S. (2017). Optical coherence tomography angiography-based capillary velocimetry. *Journal of Biomedical Optics,* 22, 66008-66013, the entire teachings of which are incorporated herein by reference), have also been demonstrated for measuring blood flow speeds.

In general, in blood flow imaging there are trade-offs between the number of OCT measurements that can be acquired, the size of field of view that can be imaged (say, 3 mm×3 mm, or 6 mm×6 mm on the retina), the transverse spatial density of the blood flow images/data, and the total imaging time. In the in vivo human eye this trade-off exists because it is highly desirable to keep imaging time to a minimum due to patient/ocular motion and patient comfort. Typically, an OCT acquisition is limited to several seconds (say, less than 5 seconds).

Flow Analysis by Merging of Multiple Integrated Spatial Samplings (FAMMISS)

To address the trade-offs described above, we propose a blood flowing imaging scheme termed flow analysis by merging of multiple integrated spatial samplings (FAMMISS). In brief, the idea behind FAMMISS is to generate data (e.g., images) having different sampling periods (defined subsequently) and then to merge this data to create data (e.g., images) pertaining to blood flow speed, velocity, or related quantities. The basic structure of the FAMMISS workflow is shown in FIG. 3.

Figure 3:
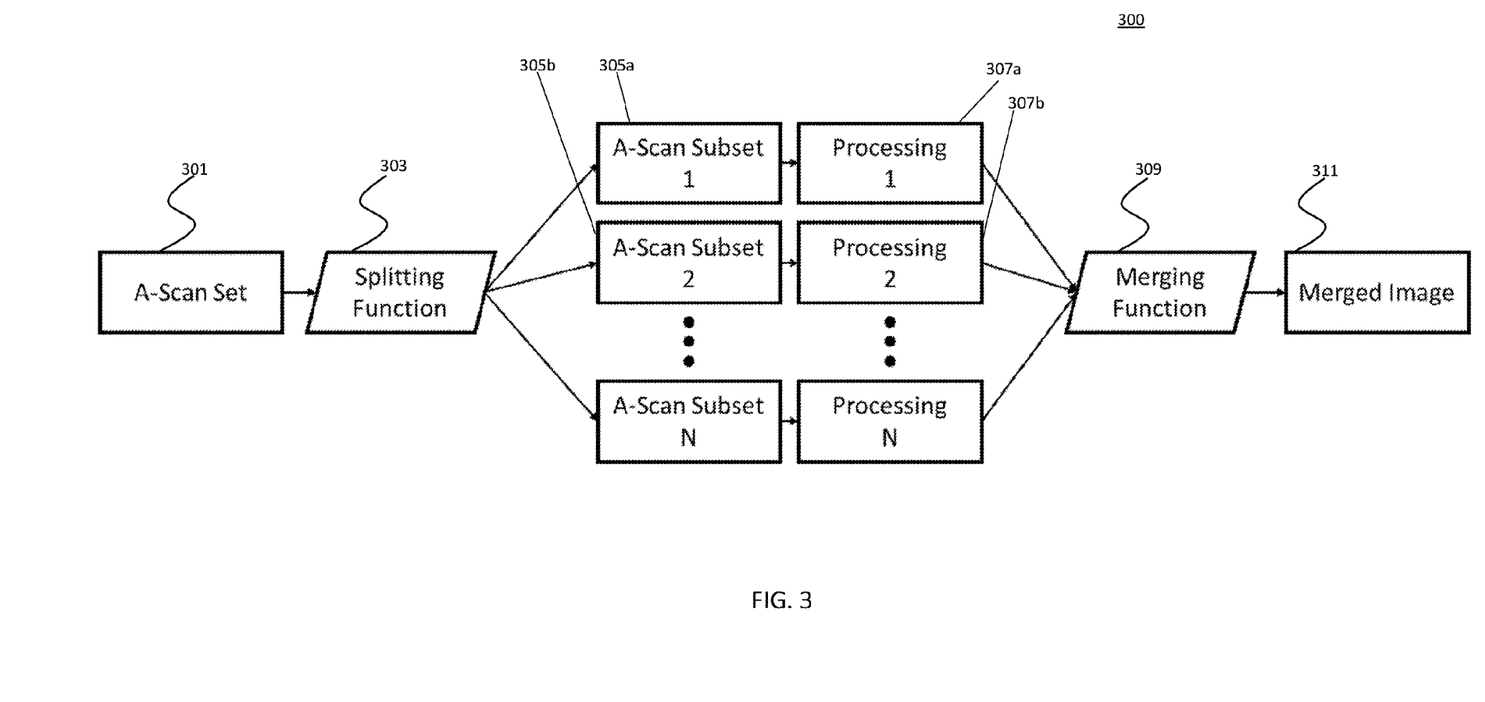
FIG. 3 is a schematic diagram illustrating an example embodiment of the present invention.
Figure 4:
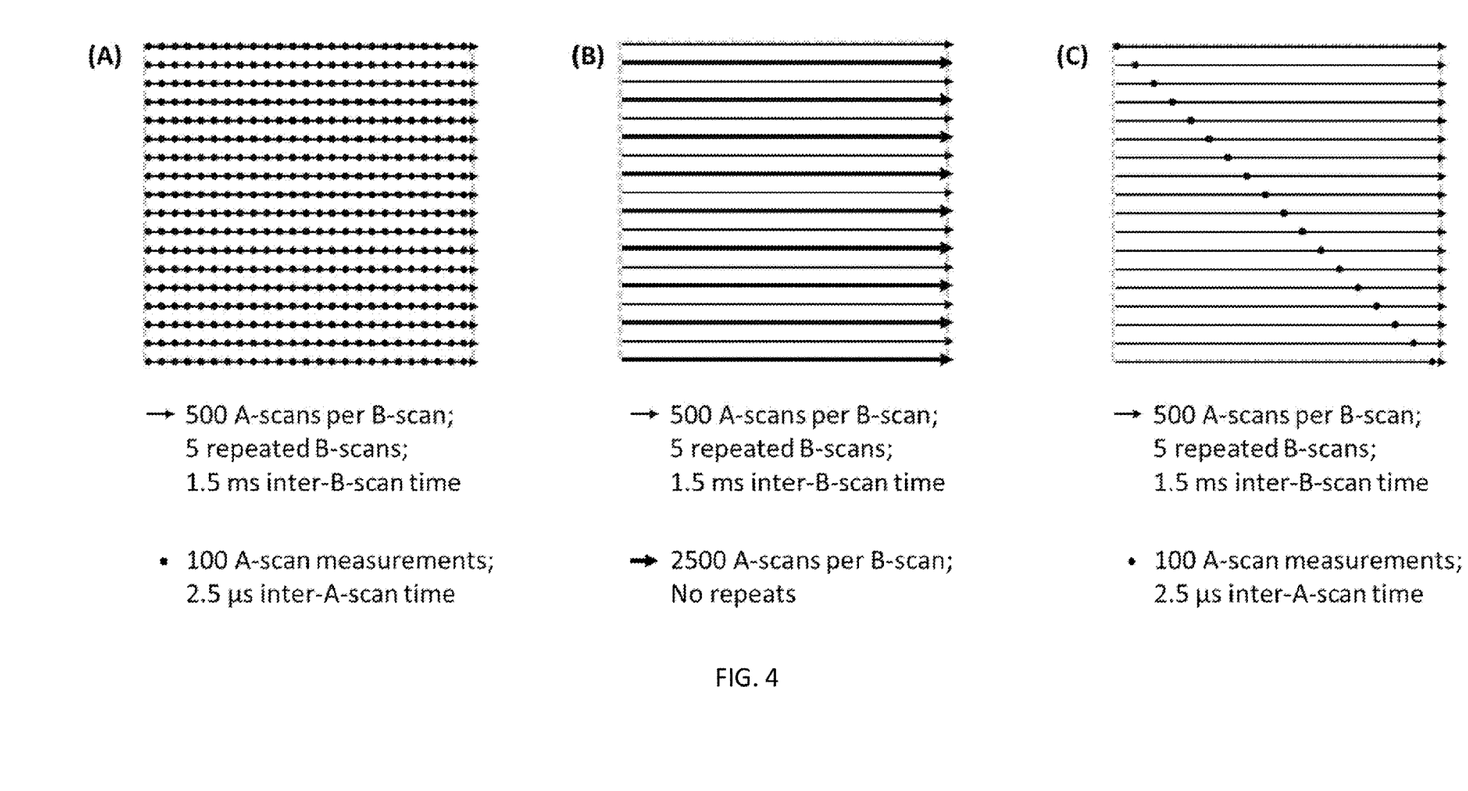
FIGS. 4(A) through 4(C) are schematic diagrams illustrating OCT data acquisition scheme that can be employed by the disclosed methods.

FIG. 3 is a schematic diagram of process 300.

In brief, a set of A-scans 301 is separated by a splitting function 303 into a set of more than one subset 305a, 305b, etc. These subsets need not be disjoint; that is, one subset may contain A-scans that are also contained in another subset. However, in one embodiment, no two subsets can have the same spatial sampling. In this embodiment, the term "same spatial sampling" means the set of positions/configurations to which beam steering apparatus is commanded. These positions are dependent on only the programmed scan pattern. In one embodiment, the spatial sampling is independent of the position of the sample being imaged. For example, if a pair of galvanometer mirrors were programmed to raster scan an OCT beam, the spatial sampling would be the set of angular configurations through which these mirrors were commanded. So, for instance, moving a patient's eye closer to, or farther from, would not constitute a different spatial sampling.

Each of A-scan subsets 305a, 305b, etc. is then processed in steps 307a, 307b, etc. to generate some image or data related to blood flow, blood flow speed, or vascular structure. Importantly, the processing blocks need not be the same. The output from each of these processing blocks is then merged in step 309 into one or more images 311, each of which displays information about blood flow speeds.

Further embodiments of process 300 will be discussed below.

Example embodiment of process 300 will now be illustrated with references to FIGS. 4 through 7.

An example of a FAMMISS processing scheme is described below with references to the A-scan scheme shown schematically in FIG. 4(A), and process 500 shown in FIG. 5. The A-scan set shown in FIG. 4(A) includes a set of A-scans from a standard OCT-A acquisition, together with a set of rapidly repeated A-scans, consistent with an DLS-OCT measurement. In particular, each solid arrow represents a 5-repeated B-scan protocol, in which each B-scan consists of 500, equally spaced, A-scans. For concreteness, we have assumed a 1.5 ms interscan time, which is consistent with a 400 kHz A-scan rate system with a ~85% galvanometer scanning duty cycle. Each solid dot represents 100 repeated A-scan measurements, where each A-scan measurement is acquired in rapid succession. Again, the 2.5 microsecond inter-A-scan time is consistent with a 400 kHz A-scan rate system.

Figure 5:
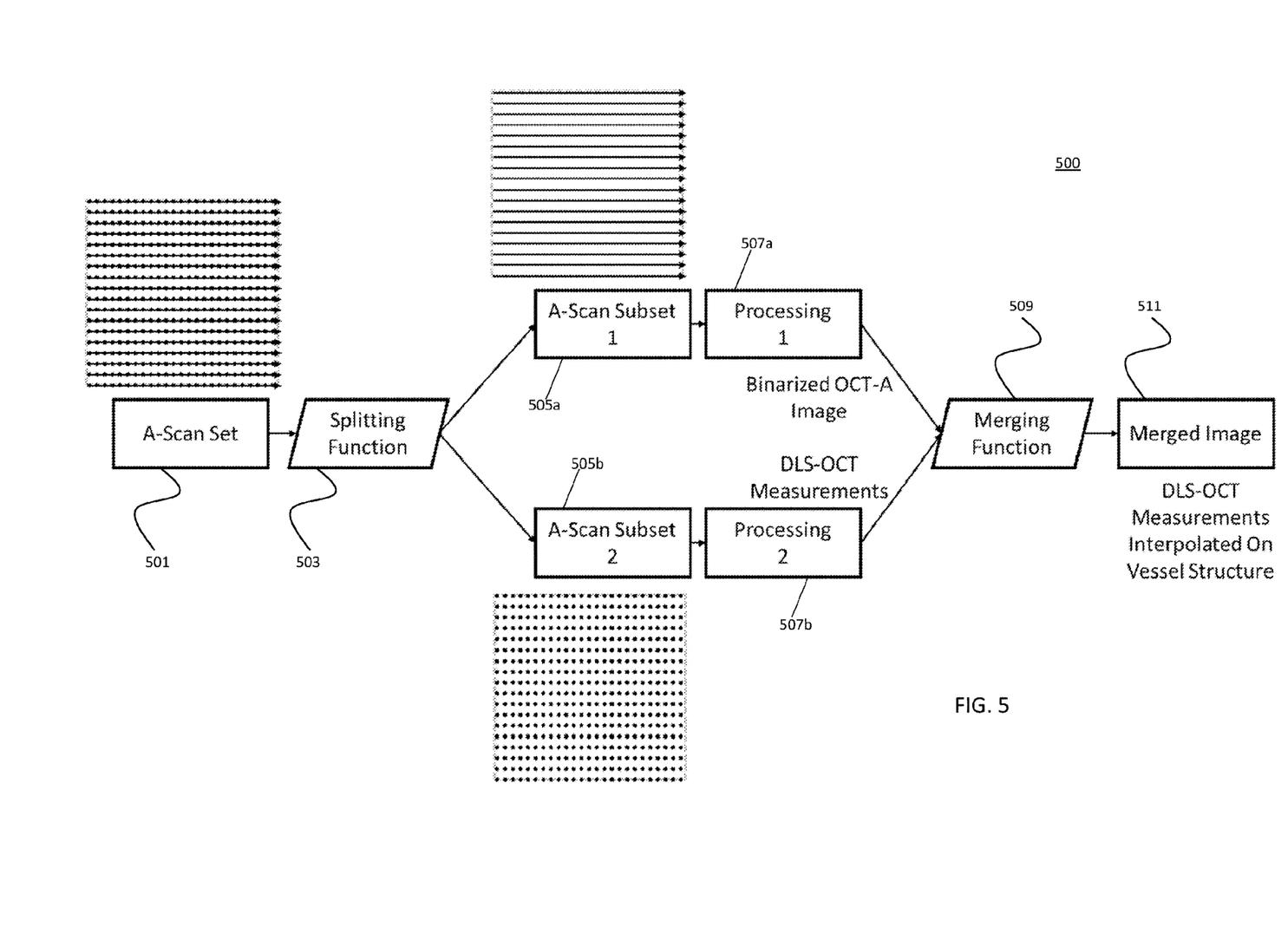
FIG. 5 is a schematic diagram illustrating an example embodiment of the present invention.

With reference to FIG. 5, in the example process 500, the A-scan set 501 is split in step 503 into a set of A-scans 505a, 505b, etc. In this example, Subset 505a is consistent with a standard OCT-A acquisition (subset 1), and a subset 505b is consistent with a DLS-OCT measurement (subset 2). In this example, in step 507a, processing block 1 performs OCT-A processing, for example using a pixel-wise decorrelation scheme, to form an output OCT-A image. In this example, this image can then be binarized, on the basis of the OCT-A signal, so that regions of blood flow (i.e., within the vasculature) are separated from regions of no/low blood flow. In step 507b, processing block 2 performs, for each of the repeated A-scan measurements (i.e., for each dot), DLS processing to estimate the blood flow speed at that location. In step 509, the merging function combines the output from the two processing blocks by interpolating the DLS-OCT blood flow speed measurements on the binarized vasculature structure and generates the merged image 511. The rationale of this FAMMISS scheme is that the DLS-OCT measurements can be spatially sparse compared to the density of the vasculature. This is important because if 100 A-scans were acquired at each of the 500 A-scan positions, with a 400 kHz A-scan rate the total acquisition time would be approximately 62.5 seconds. By reducing the DLS-OCT sampling density we can reduce the associated acquisition time. In particular, if we assume that the blood flow does not have a rapid spatially changing speed within the vessel, the interpolated DLS-OCT data can faithfully represent the true blood flow speeds. Note that this example follows the more general scheme of combining one data set that is used to derive vessel structure, and one data set that is used to derive properties (e.g., blood flow speed) of the blood flow within the vessels.

Figure 6:
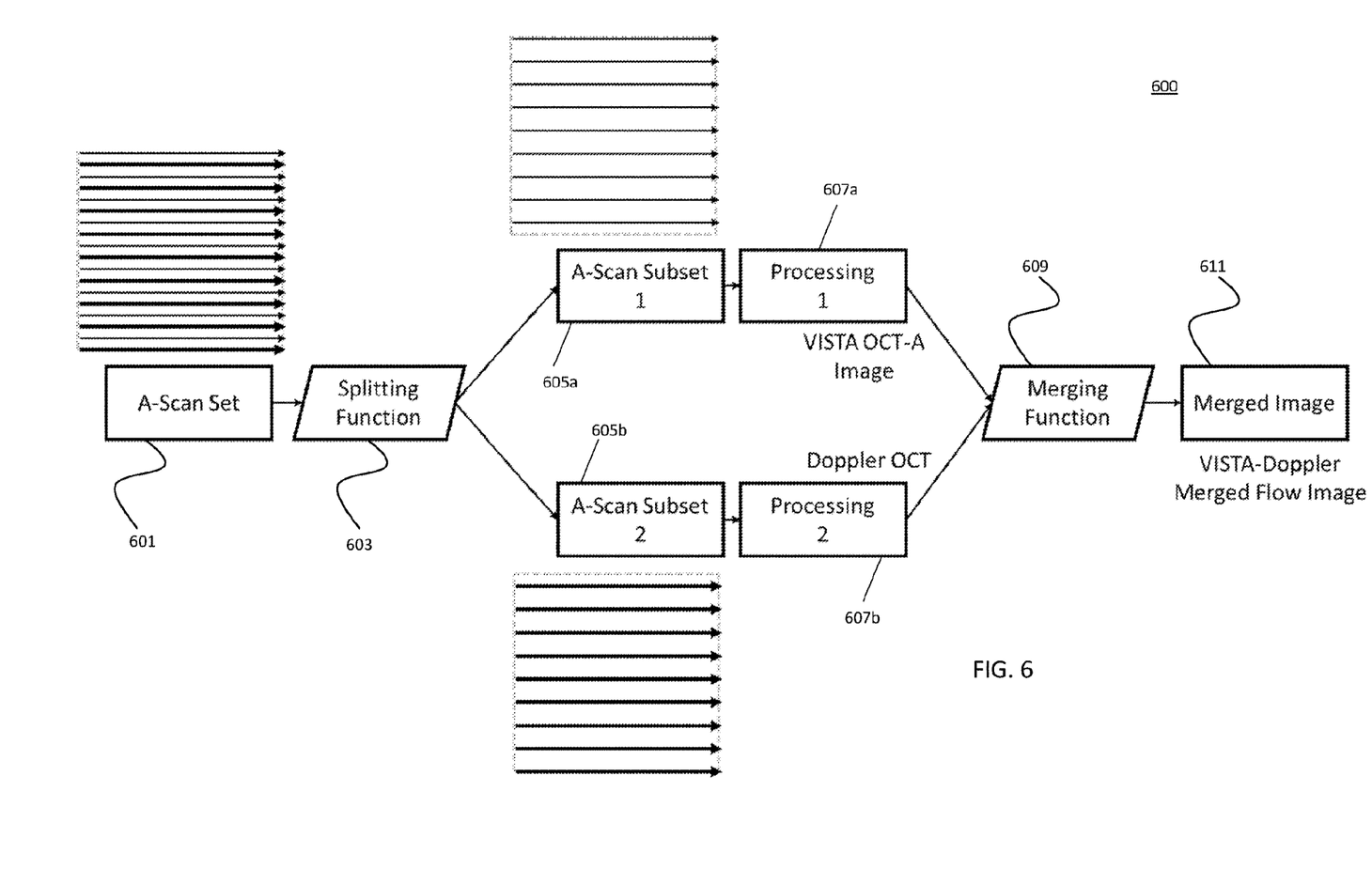
FIG. 6 is a schematic diagram illustrating an example embodiment of the present invention.

In another example embodiment, referring now to the example A-scan set shown schematically in FIG. 4(B), process 600 is illustrated in FIG. 6. The A-scan set shown in FIG. 4(B) consists of a set of A-scans from a variable interscan time analysis (VISTA) OCT-A acquisition, spatially interleaved with a set of densely acquired A-scans consistent with a Doppler OCT B-scan. Here, in the context of VISTA and repeated OCT acquisition, interscan time refers to the time it takes for the OCT beam to re-scan the same position.

In short, VISTA is an OCT-A described in details in U.S. patent application Ser. No. 15/964,917, filed on Apr. 27, 2018, incorporated herein by reference in its entirety. In VISTA, three or more repeated OCT B-scans can be partitioned into different subsets and used to estimated blood flow speeds.

In the example illustrated in FIG. 4(B), the A-scans represented by each solid, thinner arrow are consistent with those described in the prior example. In this example, each solid, thicker arrow represents a B-scan consisting of 2500, equally spaced, A-scans. The dense A-scan sampling facilitates the Doppler processing.

With reference to FIG. 6, in process 600, the A-scan set 601 is split in step 603 into a set of A-scans subsets 605a, 605b, etc. In this example, subset 605a is consistent with VISTA OCT-A acquisition (subset 1), and a subset 605b of A-scans is consistent with a DLS-OCT measurement (subset 2). In step 607a (block 1) VISTA OCT-A processing is performed. In step 607b (block 2) Doppler OCT processing is performed. In step 609, the merging function combines the output from the two processing blocks by mapping the Doppler OCT flow images into a merged image 611. In one example, merged image 611 is a merged image, in colors, of the VISTA OCT-A flow images overlaid with the Doppler OCT image in a semi-transparent manner. The rationale for such a FAMISS scheme is that the Doppler OCT and VISTA OCT-A flow images, with the given parameters, provide information about different ranges of blood flow speeds. In particular, the Doppler OCT scan will be able to better differentiate between faster blood flow speeds, while the VISTA OCT-A flow images will be able to better differentiate between slower blood flow speeds. Note that this example follows the more general scheme of combining different A-scan collections (different in the sense of spatial sampling), each of which captures different ranges/aspects of blood flow speeds, into an image, or images, which combine these different A-scan collections (or subsets thereof).

Figure 7:
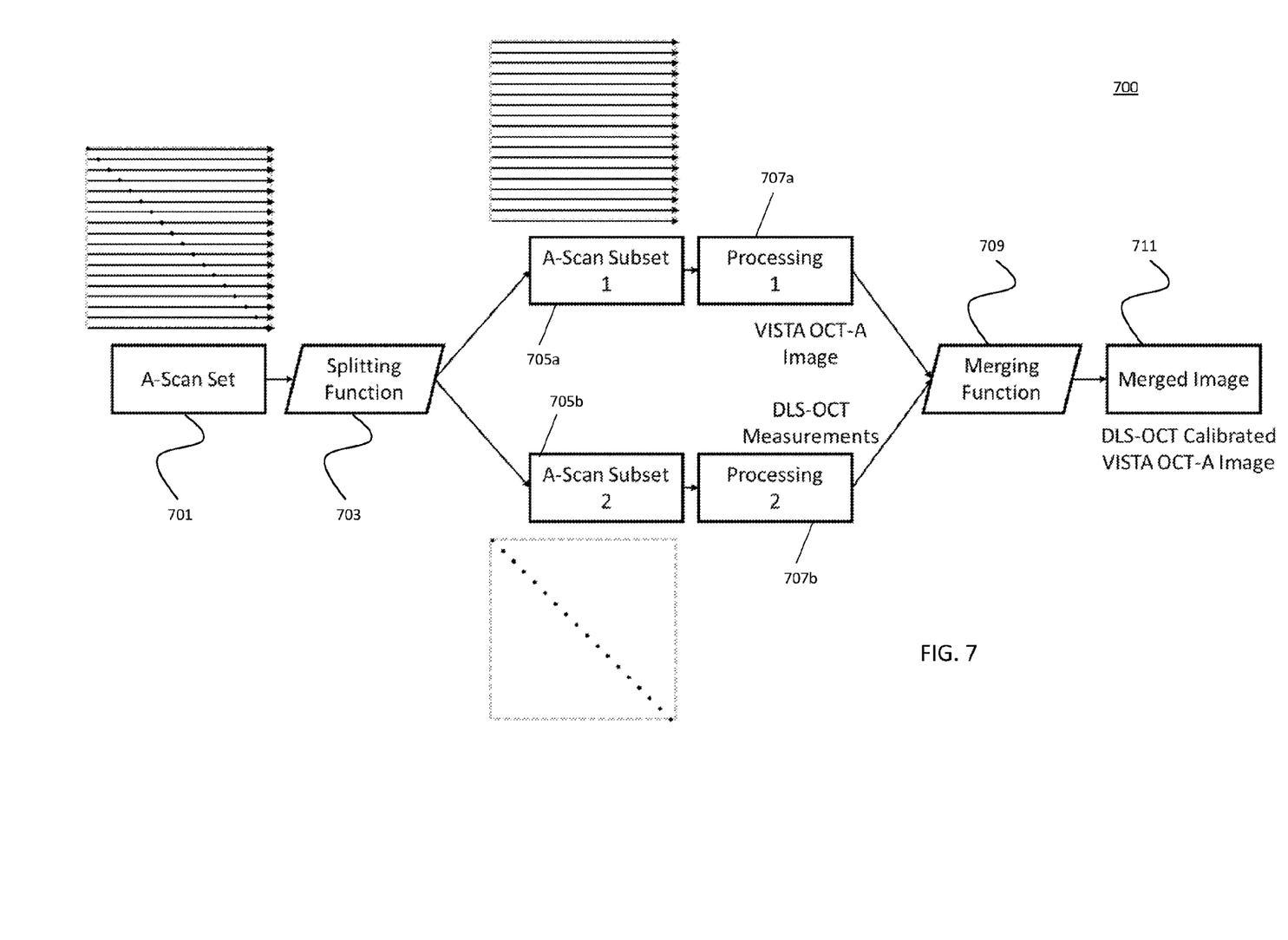
FIG. 7 is a schematic diagram illustrating an example embodiment of the present invention.

As a further example embodiment, the A-scan set is acquired as shown schematically in FIG. 4(C), and FAMISS process 700 is shown in FIG. 7.

The A-scan set shown in FIG. 4(C) consists of a set of A-scans from a VISTA OCT-A acquisition, together with a set of rapidly repeated A-scans, consistent with a DLS-OCT measurement. In this example the A-scans represented by the solid arrows and dots are consistent with those described in the prior examples.

With reference to process 700 shown in FIG. 7, the A-scan set 701 is split into a set of A-scans subsets 705a, 705b, etc. In this example, subset 705a is consistent with a VISTA OCT-A acquisition (subset 1), and a subset 705b is consistent with a DLS-OCT measurement (subset 2). In step 707a (block 1), variable interscan time analysis (VISTA) OCT-A processing is performed. In step 707b (block 2) DLS-OCT processing is performed. In step 709, the merging function combines the output from the two processing blocks into merged image 711 using the DLS-OCT measurements to calibrate the VISTA OCT-A measurements. In particular, in this example, the DLS-OCT measurements, which provide a physical speed measurement (e.g., in mm/s) can be used to associate VISTA OCT-A measurements, which may only provide relative speed measurements, with physical speeds. For example, the VISTA signal at a region coincident with, or near to, a DLS-OCT measurement could have its speed determined by that DLS-OCT measurement. By having several physical blood flow speeds for different VISTA signal levels, the blood flow speeds associated with other VISTA signal levels, for which no DLS-OCT signal was observed, could be obtained through, for example, interpolation or curve matching. Thus, the rationale for this FAMMISS scheme is that DLS-OCT measurements can be used to calibrate, in vivo, VISTA OCT-A signals. The in vivo aspect of the calibration procedure is important because, compared to, for example, bench-top validation, there are many factors that may influence how in vivo blood flow speeds generate OCT-A signals. Note that this example follows the more general scheme of combining different A-scan collections and using one or more of which to calibrate blood flow speeds on the remaining set.

It should be noted that the configurations described above are intended only as examples, and that there are many variations that fall within the scope of FAMMISS processing. Note also that we have not restricted how the initial set of A-scans is obtained. In particular, many different imaging configurations and scanning protocols may be used to generate the example. For example, in FIG. 4(C), the repeated A-scan measurements (dots) at each repeated B-scan position could be acquired by stopping the OCT beam scanning during each repeated OCT B-scan. In another embodiment, they could be acquired using a second OCT beam, that is scanned separately. In another embodiment still, they could be acquired before all repeated OCT B-scans were acquired (i.e., after all B-scans from all B-scans positions were acquired). In this case it could, for example, be desirable to register these different datasets because they may be spatially misaligned due to, for example, patient motion. This registration could, for example, be performed using blood flow information and/or structural information, or could be achieved by implementing special registration patterns, for example scanning a cross, or circle, covering the field of view, immediately before the acquisition of each set of A-scans. Other modalities, for example, scanning laser ophthalmoscopy (SLO), or fundus photography, could also be used to spatially register these data sets. Furthermore, note that the A-scan sets acquired for FAMMISS need not be acquired in a single acquisition; multiple acquisitions may be used. With multiple acquisitions, spatial registration would be especially important.

Corresponding System and Scanning Protocols

A system for implementing the above methods comprises an OCT scanner that is configured to acquire a set, or sets, of OCT A-scans in a manner consistent with FAMMISS processing; a processor configured to perform the above calculations and processing of the images; a display configured to process and display the resulting images as a color-coded image, or image(s) (e.g., as a volume, orthoplane volume, en face image, or B-scan image). The OCT scanner may have a 1,050 nm, 400 kHz A-scan rate, and be a swept source OCT system. Galvanometer scanning mirrors or resonant scanning mirrors may be used.

The OCT system used may have vertical cavity surface emitting laser (VCSEL) or other frequency swept laser sources, for example, a Fourier-domain mode locked (FDML) laser. Frequency comb or akinetic light sources may also be used. The light sources may have narrow linewidths and high sweep rates, and may be centered at a 1,050 nm wavelength. The 1,050 nm center wavelength, when compared with the 840 nm wavelength systems, enables deeper light penetration into the retinal pigment epithelium, choroid, and reduced attenuation from ocular opacities. Other wavelengths, for example, 1,310 nm, may be used, for example, for anterior eye imaging, or imaging of other tissues. Other light sources, such as super luminescent diodes, either at 840 nm wavelengths, or other wavelengths, may also be used. Spectral-domain OCT (SD-OCT) or swept-source OCT (SS-OCT) configurations may be used. The choice of light-source may be determined by a combination of axial resolution, beam absorption, scan rate, phase-stability, the type of tissues being imaged, and/or other factors.

For swept-source OCT configurations, the OCT interferometric signals can be acquired with an analog-to-digital acquisition card externally clocked at a maximum frequency of 1.1 GHz using an external Mach-Zehnder interferometer. Faster or slower clock rates may also be used. A fiber Bragg grating (FBG) may be used to stabilize the phase of the sweep. Other phase stabilization methods, such as placing reflectors in the reference and/or sample arms may be used. The card may also be clocked internally, with the signal being re-sampled linearly in wavenumber in post-processing. The signal may be collected in a polarization sensitive, or diverse configuration, and quadrature and phase information may also be detected.

The fields of view over which imaging is performed may range in size, but may, for example, include 12 mm×12 mm, 9 mm×9 mm, 6 mm×6 mm, or 3 mm×3 mm, 1.5 mm×1.5 mm, or 1.0 mm×1.0 mm fields of view. Multiple field sizes may be acquired and then stitched together in post-processing, and/or eye tracking may be used to help inform the stitching. En face OCT imaging, or imaging of another modality, such as fundus photography or scanning laser ophthalmoscopy, may be used to guide the placement of the imaging fields, and/or to detect and compensate for motion. This information may be connected to the beam scanning apparatus in an open or closed loop configuration. The system user may select particular features, or regions, of the eye onto which to focus the scan area. This selection may be performed using OCT information, or information from another modality. It may be possible to adjust, either manually or automatically, the scanning protocol on the basis of the scanning field size, type of lesion being imaged, type of analysis that the system wishes to perform, or other factors.

A processor of the OCT system, or of for example, a computer which receives an output of the OCT system, can be used to perform the above described computations and generate the above-described displays and images. The aspects described herein may be implemented on a processor or a plurality of processors, such as a graphics processing unit (GPU) or similar dedicated graphics processor. These processor(s) also may be embedded or integrated with other processors designed for a separate purpose, for example, as part of a central processing unit (CPU). Such processor(s) may also be for general-purpose computing on a graphics processor unit (GPGPU). A "processor" as used herein refers to any, or part of any, electrical circuit comprised of any number of electrical components, including, for example, resistors, transistors, capacitors, inductors, and the like. The circuit may be of any form, including, for example, an integrated circuit, a set of integrated circuits, a microcontroller, a microprocessor, a collection of discrete electronic components on a printed circuit board (PCB) or the like. The processor may also stand alone or be part of a computer used for operations other than processing image data. Implementation of these aspects by hardware or software may be realized in any number of electronic devices and/or applications, including but not limited to, personal computers, servers, integrated OCT or similar imaging machines, and the like. Moreover, the above aspects and/or combination of aspects may be stored in memory which is executable by one of said processors. It should also be noted that the above description is non-limiting, and the examples are but only a few of many possible processors and implementations envisioned.

It is to be noted that any of the aspects or combination of aspects described herein may be implemented via hardware or software.

Advantages of the Methods Described Herein

The ability to visualize blood flow speed changes—as opposed to simply the presence or absence of blood flux—can be valuable for studying a variety of ocular diseases. This can be particularly true for those whose pathogenesis proceeds through different stages of flow impairment rather than an immediate progression to total vascular atrophy.

Images generated according to the above methods and systems can, for example, be used to investigate markers for disease progression, or early disease detection. Typical OCT-A methods provide limited information about blood flow speed. In general, for OCT based blood flow measurements in the eye there are trade-offs between the number of OCT measurements that can be acquired, the size of field of view that can be imaged (say, 3 mm×3 mm, or 6 mm×6 mm on the retina), the transverse spatial density of the blood flow images/data, and the total imaging time. In the in vivo human eye this trade-off exists because it is highly desirable to keep imaging time to a minimum, because of patient and ocular motion, and also because of patient comfort. To address these limitations, we propose the FAMMISS processing scheme. We also present three particular sub-classes of FAMMISS processing: (1) combining one data set that is used to derive vessel structure, and one data set that is used to derive properties (e.g., blood flow speed) of the blood flow within the vessels; (2) combining different A-scan collections (different in the sense of spatial sampling), each of which captures different ranges/aspects of blood flow speeds, into an image, or images, which combine these different A-scan collections (or subsets thereof); and (3) combining different A-scan collections and using one or more of which to calibrate blood flow speeds on the remaining set.

FURTHER EMBODIMENTS

The embodiments and examples embodiments of the methods and systems disclosed herein will be further explained in paragraphs below.

As used herein, a three-dimensional (3D) OCT data set is an array of elements, each element representing an OCT signal obtained from a point in 3D space at a point in time.

As used herein, the term "repeated measurement" refers to an element of a 3D OCT data set that represents an OCT signal obtained from a point in space that is spatially coincident with (has the same 3D coordinates as) at least one other point in space from which an OCT signal was obtained at a different time. In other words, two or more "repeated measurements" are two or more values of OCT signal obtained from the same point in space at different times.

As used herein, the term "non-repeated measurement" refers to an element of a 3D OCT data set that is not a repeated measurement.

For any repeated measurement, the term "sampling period" is the minimum absolute difference in time between this repeated measurement and all other OCT signals obtained from the same point in space.

For any non-repeated measurement, the term "sampling period" is the minimum absolute difference in time between the point in space corresponding to this non-repeated measurement and all other elements of the OCT data set.

As used herein, the term "composite image" refers to an image that is constructed from two or more different images or two or more data sets that each can be used to generate an image.

As used herein, the term "imaging modality" refers to any method, process or algorithm that can be used to generate an image, for example, a medical image suitable for use by a trained clinician, based on an OCT data set.

"Processing" a data set according to an imaging modality means applying a method, process or algorithm implementing this imaging modality to a data set of interest.

As used herein, the term "data subset" refers to a set of data all elements of which are belong to its corresponding data set. For example, a data subset, can be smaller than its corresponding data set. In another example, a data subset can be equal to its corresponding data set.

In a first example embodiment, the present invention is a computer-implemented method of imaging an object. In a first aspect of the first example embodiment, the method comprises acquiring a three-dimensional optical coherence tomography (OCT) data set representing an object, wherein the OCT data set includes at least a first and a second three-dimensional data subsets, each element of the OCT data set having a respective sampling period, wherein at least a first element of the first data subset represents a point in space that is not represented by any element of the second subset, and at least one element of the second subset has a sampling period different from the sampling period of the first element of the first subset; processing at least the first and the second data subsets according to at least one imaging modality, thereby generating at least a first and a second processed data subsets, each processed data subset representing the object; and generating a composite image representing the object based on at least the first and the second processed data sub sets.

In a second aspect of the first example embodiment, the method further includes displaying the composite image.

In a third aspect of the first example embodiment, acquiring the three-dimensional OCT data set includes obtaining said data set from a data storage device. For example, in the third aspect of the first example embodiment, at least the first and the second data subsets can be registered to a fiducial marker.

In a fourth aspect of the first example embodiment, acquiring the three-dimensional OCT data set includes acquiring said data with an Optical Coherence Tomography (OCT) imaging instrument.

Examples of imaging modalities suitable for practicing the first example embodiment include one or more of OCT-dynamic light scattering (DLS), Doppler OCT, and VISTA OCT, OCT Angiography Ratio Analysis (OCTARA), split-spectrum amplitude-decorrelation angiography (SSADA) (see, e.g., Jia, Y., Tan, O., Tokayer, J., Potsaid, B., Wang, Y., Liu, J. J., Huang, D. (2012). Split-Spectrum Amplitude-Decorrelation Angiography with Optical Coherence Tomography. *Optics Express*, 20(4), 4710-4725, the entire teachings of which are incorporated herein by reference), optical microangiography (OMAG) and its derivatives (see, e.g., An, L., Qin, J., & Wang, R. K. (2010). Ultrahigh sensitive optical microangiography for in vivo imaging of microcirculations within human skin tissue beds. *Optics Express*, 18(8), 8220-8228, the entire teachings of which is incorporated herein by reference), eigenvalue decomposition-based velocimetry (see, e.g., Wang, R. K., Zhang, Q., Li, Y., & Song, S. (2017). Optical coherence tomography angiography-based capillary velocimetry. *Journal of Biomedical Optics*, 22, 66008-66013, the entire teachings of which are incorporated herein by reference in its entirety), or phase variance angiography (see, e.g., Fingler, J., Schwartz, D., Yang, C., & Fraser, S. E. (2007). Mobility and transverse flow visualization using phase variance contrast with spectral domain optical coherence tomography. *Optics Express*, 15(20), 12636-12653, the entire teachings of which are incorporated herein by reference).

In a fifth aspect of the first example embodiment, at least one imaging modality is VISTA OCT. In this aspect, the three dimensional OCT data set includes data representing at least three B-scans of a same location of an object, the B-scans separated by one or more interscan time intervals.

In a sixth aspect of the first example embodiment, the object is associated with a patient. Examples of such objects can include an eye, retina, fovea, optic nerve head, choroid and/or choriocapillaris, or cornea.

In a seventh aspect of the first example embodiment, the object includes fluid flowing therethrough.

In an eighth aspect of the first example embodiment, the composite image represents the flow of the fluid through the object.

In a ninth aspect of the first example embodiment, the object includes vasculature and blood flowing therethrough.

In an example embodiment of the ninth aspect of the first embodiment, the first processed data subset represents the vasculature, and the second processed data subset represents one of blood flow, blood oxygenation, hematocrit, presence of particular immune cells or inflammatory markers, elements of a complete blood count (CBC), blood flow speed/velocity, blood flow turbulence.

In various example embodiments of the sixth through ninth aspects of the first example embodiment, the patient can be suffering from an ocular disease, such as an abnormal vasculature or a microaneurysm.

In a second example embodiment, the present invention is an optical coherence tomography (OCT) imaging system. In a first aspect of the second example embodiment, the system comprises: a memory configured to store a three-dimensional optical coherence tomography (OCT) data set representing an object, wherein the OCT data set includes at least a first and a second three-dimensional data subsets, each element of the OCT data set having a respective sampling period, wherein at least a first element of the first data subset represents a point in space that is not represented by any element of the second subset, and at least one element of the second subset has a sampling period different from the sampling period of the first element of the first subset; a computing module, configured to process at least the first and the second data subsets according to at least one imaging modality, and thereby to generate at least a first and a second processed data subsets, each processed data subset representing the object; and to generate a composite image representing the object based on at least the first and the second processed data subsets.

In a second aspect of the second example embodiment, the system further includes a display module configured to display the composite image.

In a third aspect of the second example embodiment, the system further includes a data acquisition module comprising an optical coherent tomography (OCT) imaging instrument, the data acquisition module configured to acquire the three-dimensional OCT data set representing an object, wherein the OCT data set includes at least the first and the second three-dimensional data subsets, each element of the OCT data set having the respective sampling period, wherein the sampling period of at least one element of the first data subset is different from the sampling period of at least one element of the second data subset.

In a fourth aspect of the second example embodiment, the memory is configured to receive the three-dimensional OCT data set includes obtaining said data set from a data storage device. In this aspect, for example, at least the first and the second data subsets can be registered to a fiducial marker.

In various aspects of the second example embodiment, the system is configured to implement the methods described above with respect to the various aspects of the first example embodiment.

In a third example embodiment, the present invention is a non-transitory computer-readable medium having thereon a sequence of instructions. In a first aspect of the third example embodiment, the instructions, when executed by a processor: cause a memory to store a three-dimensional optical coherence tomography (OCT) data set representing an object, wherein the OCT data set includes at least a first and a second three-dimensional data subsets, each element of the OCT data set having a respective sampling period, wherein at least a first element of the first data subset represents a point in space that is not represented by any element of the second subset, and at least one element of the second subset has a sampling period different from the sampling period of the first element of the first subset; cause a computing module to process at least the first and the second data subsets according to at least one imaging modality, thereby generating at least a first and a second processed data subsets, each processed data subset representing the object; and to generate a composite image representing the object based on at least the first and the second processed data sub sets.

In a second aspect of the third example embodiment, the medium further includes a sequence of instructions, which, when executed by the processor, cause a display module to display the composite image.

In a third aspect of the third example embodiment, the medium further includes a sequence of instructions, which, when executed by the processor, cause a data acquisition module comprising an optical coherent tomography (OCT) imaging instrument to acquire the three-dimensional OCT data set representing an object, wherein the OCT data set includes at least the first and the second three-dimensional data subsets, each element of the OCT data set having the respective sampling period, wherein the sampling period of at least one element of the first data subset is different from the sampling period of at least one element of the second data subset.

In a fourth aspect of the third example embodiment, the medium further includes a sequence of instructions, which, when executed by the processor, cause the memory to receive the three-dimensional OCT data set includes obtaining said data set from a data storage device.

In a fourth example embodiment, the present invention is a computer-implemented method of imaging an object. In a first aspect of the fourth example embodiment, the method comprises acquiring a three-dimensional optical coherence tomography (OCT) data set representing an object, each element of the OCT data set having a respective sampling period, wherein the sampling period of at least a first element of the data set is different from the sampling period of at least a second element of the data set; and generating an image representing the object based on at least the first and the second elements.

In a second aspect of the fourth example embodiment, the method further includes displaying the generated image.

Various further aspects of the fourth example embodiment are described above with respect to the first example embodiments and aspects thereof.

In a fifth example embodiment, the present invention is an optical coherent tomography (OCT) imaging system. In a first aspect of the fifth example embodiment, the system comprises a memory configured to store a three-dimensional optical coherence tomography (OCT) data set representing an object, each element of the OCT data set having a respective sampling period, wherein the sampling period of at least a first element of the data set is different from the sampling period of at least a second element of the data set;

and a computing module configured to generate an image representing the object based on at least the first and the second elements.

In a second aspect of the fifth example embodiment, the system further includes a display module configured to display the generated image.

Various further aspects of the fifth example embodiment are described above with respect to the second example embodiments and aspects thereof.

In a sixth example embodiment, the present invention is a non-transitory computer-readable medium having thereon a sequence of instructions, which, when executed by a processor, cause a memory configured to store a three-dimensional optical coherence tomography (OCT) data set representing an object, each element of the OCT data set having a respective sampling period, wherein the sampling period of at least a first element of the data set is different from the sampling period of at least a second element of the data set; and cause a computing module configured to generate an image representing the object based on at least the first and the second elements.

Various further aspects of the sixth example embodiment are described above with respect to the third example embodiments and aspects thereof.

While this disclosure is based on the OCT imaging modality, it is not limited to OCT. For example, it is applicable to ultrasound as well. It should also be noted that while the technique described herein is related to angiography for retinal and choroidal vessel visualization, the technique is not limited in this manner either; rather, it may be applied to other visualizations of the eye (for example, visualization of vasculature in the anterior eye), or of other organs, for example in endoscopic applications, or in cardiology applications, or for studying the reperfusion of kidneys, or for evaluating the success of vascular anastomoses. The technique may also be applied to study the speed of other biological fluids besides blood, for example, the fluid of the lymphatic system.

While this invention has been particularly shown and described with references to example embodiments thereof, it will be understood by those skilled in the art that various changes in form and details may be made therein without departing from the scope of the invention encompassed by the appended claims.

What is claimed is:

1. A computer-implemented method of imaging an object, the method comprising:
acquiring a three-dimensional optical coherence tomography (OCT) data set representing an object, wherein the OCT data set includes at least a first and a second three-dimensional data subsets, each element of the OCT data set having a respective sampling period, wherein at least a first element of the first data subset represents a point in space that is not represented by any element of the second subset, and at least one element of the second subset has a sampling period different from the sampling period of the first element of the first subset;
processing at least the first and the second data subsets according to at least one imaging modality, thereby generating at least a first and a second processed data subsets, each processed data subset representing the object; and
generating a composite image representing the object based on at least the first and the second processed data subsets,
wherein the object includes a patient's vasculature and blood flowing therethrough, and
wherein the first processed data subset represents the vasculature, and the second processed data subset represents blood flow, blood oxygenation, hematocrit, presence of particular immune cells or inflammatory markers, elements of a complete blood count (CBC), blood flow speed/velocity, blood flow turbulence.

2. The method of claim 1, further including displaying the composite image.

3. The method of claim 1, wherein acquiring the three-dimensional OCT data set includes obtaining said data set from a data storage device.

4. The method of claim 3, wherein at least the first and the second data subsets are registered to a fiducial marker.

5. The method of claim 1, wherein acquiring the three-dimensional OCT data set includes acquiring said data with an Optical Coherence Tomography (OCT) imaging instrument.

6. The method of claim 1, wherein at least one imaging modality is OCT-dynamic light scattering (DLS).

7. The method of claim 1, wherein the three dimensional OCT data set includes data representing at least three B-scans of a same location of an object, the B-scans separated by one or more interscan time intervals.

8. The method of claim 7, wherein at least one imaging modality is one of VISTA-OCT.

9. The method of claim 1, wherein at least one imaging modality is OCT-dynamic light scattering (DLS), Doppler OCT, OCT Angiography Ratio Analysis (OCTARA), split-spectrum amplitude-decorrelation angiography (SSADA), optical microangiography (OMAG), eigenvalue decomposition-based velocimetry, or phase variance angiography.

10. The method of claim 1, wherein the object is one of eye, retina, fovea, optic nerve head, choroid and/or choriocapillaris, or cornea.

11. The method of claim 1, wherein the patient is suffering from an ocular disease.

12. The method of claim 1, wherein the patient is suffering from an abnormal vasculature.

13. The method of claim 1, wherein the patient is suffering from a microaneurysm.

14. An optical coherent tomography (OCT) imaging system comprising:
a memory configured to store a three-dimensional optical coherence tomography (OCT) data set representing an object, wherein the OCT data set includes at least a first and a second three-dimensional data subsets, each element of the OCT data set having a respective sampling period, wherein at least a first element of the first data subset represents a point in space that is not represented by any element of the second subset, and at least one element of the second subset has a sampling period different from the sampling period of the first element of the first subset;
a computing module, configured to process at least the first and the second data subsets according to at least one imaging modality, and thereby to generate at least a first and a second processed data subsets, each processed data subset representing the object;
and to generate a composite image representing the object based on at least the first and the second processed data subsets,
wherein the object includes a patient's vasculature and blood flowing therethrough, and
wherein the first processed data subset represents the vasculature, and the second processed data subset represents blood flow, blood oxygenation, hematocrit, presence of particular immune cells or inflammatory markers, elements of a complete blood count (CBC), blood flow speed/velocity, blood flow turbulence.

15. The system of claim 14, further including a display module configured to display the composite image.

16. The system of claim 14, further including a data acquisition module comprising an optical coherent tomography (OCT) imaging instrument, the data acquisition module configured to acquire the three-dimensional OCT data set representing an object, wherein the OCT data set includes at least the first and the second three-dimensional data subsets, each element of the OCT data set having the respective sampling period, wherein the sampling period of at least one element of the first data subset is different from the sampling period of at least one element of the second data subset.

17. The system of claim 14, wherein the memory is further configured to receive the three-dimensional OCT data set from a data storage device.

18. The system of claim 17, wherein at least the first and the second data subsets are registered to a fiducial marker.

19. The system of claim 14, wherein the three dimensional OCT data set includes data representing at least three B-scans of a same location of an object, the B-scans separated by one or more interscan time intervals.

20. The system of claims 19, wherein at least one imaging modality is VISTA OCT.

21. The system of claim 14, wherein at least one imaging modality is one of OCT-dynamic light scattering (DLS), Doppler OCT, OCT Angiography Ratio Analysis (OCT-ARA), split-spectrum amplitude-decorrelation angiography (SSADA), optical microangiography (OMAG) and its derivatives, eigenvalue decomposition-based velocimetry, or phase variance angiography.

* * * * *